(12) United States Patent
Netabayashi et al.

(10) Patent No.: US 10,881,373 B2
(45) Date of Patent: Jan. 5, 2021

(54) X-RAY CT APPARATUS

(71) Applicant: TOSHIBA MEDICAL SYSTEMS CORPORATION, Otawara (JP)

(72) Inventors: Tomoyuki Netabayashi, Nasushiobara (JP); Hirotaka Ujiie, Otawara (JP); Kazuki Gatayama, Otawara (JP); Atsushi Fukano, Otawara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 139 days.

(21) Appl. No.: 15/685,100

(22) Filed: Aug. 24, 2017

(65) Prior Publication Data

US 2018/0070908 A1 Mar. 15, 2018

(30) Foreign Application Priority Data

Sep. 13, 2016 (JP) .................................. 2016-178235

(51) Int. Cl.
*A61B 6/00* (2006.01)
*A61B 6/03* (2006.01)
*A61B 6/06* (2006.01)

(52) U.S. Cl.
CPC .............. *A61B 6/544* (2013.01); *A61B 6/032* (2013.01); *A61B 6/4035* (2013.01); *A61B 6/4447* (2013.01); *A61B 6/488* (2013.01); *A61B 6/503* (2013.01); *A61B 6/541* (2013.01);

(Continued)

(58) Field of Classification Search
CPC ......... A61B 6/032; A61B 6/06; A61B 6/4035; A61B 6/4447; A61B 6/488; A61B 6/503; A61B 6/541; A61B 6/542; A61B 6/544; A61B 6/545
See application file for complete search history.

(56) References Cited

U.S. PATENT DOCUMENTS 4,259,725 A * 3/1981 Andrews ................ A61B 6/032
715/856
5,754,623 A * 5/1998 Seki ...................... A61N 5/1042
378/65

(Continued)

FOREIGN PATENT DOCUMENTS

JP 5-176921 A 7/1993
JP 2005-20338 A 1/2005

(Continued)

OTHER PUBLICATIONS

Japanese Office Action dated Jul. 14, 2020 in Japanese Patent Application No. 2016-178235, 4 pages.

*Primary Examiner* — Marcus H Taningco
(74) *Attorney, Agent, or Firm* — Oblon, McClelland, Maier & Neustadt, L.L.P.

(57) ABSTRACT

In one embodiment, An X-ray CT apparatus includes: a rotating body and processing circuitry configured to extract an anatomical landmark from a medical image of an object acquired by a first scan, identify a shape of an anatomical site of the object based on the anatomical landmark, and set scanning conditions of a second scan based on the shape of the anatomical site, the second scan including a tilt scan in which a scan is performed under a condition where the rotating body is tilted, the scanning conditions including at least a tilt angle of the tilt scan.

11 Claims, 12 Drawing Sheets

(52) U.S. Cl.
CPC .............. *A61B 6/542* (2013.01); *A61B 6/545* (2013.01); *A61B 6/06* (2013.01)

(56) References Cited

U.S. PATENT DOCUMENTS

| | | | | |
|---|---|---|---|---|
| 7,391,846 | B2* | 6/2008 | Verdonck | A61B 6/4441 378/62 |
| 2005/0207526 | A1* | 9/2005 | Altman | A61B 6/032 378/20 |
| 2007/0019781 | A1* | 1/2007 | Haras | A61B 6/02 378/4 |
| 2008/0013678 | A1* | 1/2008 | Magerl | A61B 90/50 378/20 |
| 2008/0123924 | A1* | 5/2008 | Nabatame | G06T 7/0012 382/131 |
| 2008/0226022 | A1* | 9/2008 | Akino | G06T 11/005 378/15 |
| 2009/0147909 | A1* | 6/2009 | Yoda | A61B 6/032 378/4 |
| 2011/0288407 | A1* | 11/2011 | Brinks | A61B 6/032 600/427 |
| 2012/0035463 | A1* | 2/2012 | Pekar | A61N 5/103 600/411 |
| 2014/0219416 | A1* | 8/2014 | Kimoto | G06T 11/003 378/8 |
| 2014/0253544 | A1* | 9/2014 | Arakita | A61B 6/032 345/419 |
| 2015/0104092 | A1* | 4/2015 | Flohr | G06K 9/4604 382/131 |
| 2015/0228070 | A1* | 8/2015 | Birkbeck | G06T 7/0012 382/131 |
| 2015/0297157 | A1 | 10/2015 | Mukumoto | |
| 2017/0143292 | A1* | 5/2017 | Yun | A61B 6/032 |
| 2018/0160989 | A1* | 6/2018 | Herrmann | H01L 27/14676 |
| 2018/0184997 | A1* | 7/2018 | Tsukagoshi | A61B 5/055 |
| 2018/0289352 | A1* | 10/2018 | Grass | A61B 6/027 |

FOREIGN PATENT DOCUMENTS

| | | |
|---|---|---|
| JP | 2015-150220 A | 8/2015 |
| JP | 2015-213749 | 12/2015 |

* cited by examiner

US 10,881,373 B2

X-RAY CT APPARATUS

CROSS-REFERENCE TO RELATED APPLICATION

This application is based upon and claims the benefit of priority from Japanese Patent Application No. 2016-178235, filed on Sep. 13, 2016, the entire contents of which are incorporated herein by reference.

FIELD

Embodiments described herein relate generally to an X-ray CT (Computed Tomography) apparatus.

BACKGROUND

An X-ray CT apparatus is a medical image diagnostic apparatus which acquires projection data of an object from plural angles by rapidly rotating an X-ray source about the object placed on a table. An X-ray CT apparatus generates a two-dimensional CT image and/or a three-dimensional CT image by reconstructing plural projection data acquired for respective angles.

In a scan mode called a helical scan, relative positional relationship between an X-ray source and an object is changed while the X-ray source is being continuously rotated, and projection data of the whole body of the object can be acquired by one scan. In the present specification, it is assumed that a scan is processing of generating projection data by radiating and detecting X-rays and does not include image reconstruction processing. When an object is imaged by using an X-ray CT apparatus, the object is generally placed on a table such that the body axis direction (i.e., head-to-foot direction) of the object is along the longitudinal direction of the table (i.e., the z-axis direction of the apparatus coordinate system described below) and a scan is performed while the table is being moved in the z-axis direction.

Since multi-row structure of an X-ray detector has been advanced and detection elements constituting an X-ray detector have improved in performance in recent years, a range of detecting X-rays in one X-ray irradiation has been improved. For instance, in the case of an X-ray CT apparatus equipped with an X-ray detector which includes detection elements arranged in 320 rows in the z-axis direction of the apparatus coordinate system (i.e., the slice direction), it is possible to image a range having a width of 16 cm in the z-axis direction by a rotational scan. Incidentally, an object is usually placed on a table such that its body-axis direction matches the z-axis direction.

The above-described rotational scan is a scan mode in which an X-ray source is rotated about an object by 360 degrees or by 180 plus α degrees. Since a rotational scan has improved in wideness of an imaging range as described above, it is possible to perform imaging under a rotational scan in a shorter time with lower exposure dose than a helical scan.

In an examination using an X-ray CT apparatus, a prescan for acquiring projection data of a scanogram image is performed prior to a main scan in which projection data of medical images for image diagnosis are acquired. A scanogram image is an image acquired with low exposure dose prior to a main scan in order to determine imaging conditions of the main scan such as exposure dose and an imaging range.

When exposure dose is reduced in imaging with the use of an X-ray CT apparatus, it increases the possibility that image quality is deteriorated. However, it is preferable to minimize exposure dose within a range where satisfactory image quality is maintained in terms of precise diagnosis. Thus, it has been desired to provide technology to automatically set imaging conditions by which predetermined image quality is maintained and exposure dose is minimized.

DETAILED DESCRIPTION

Figure 1:
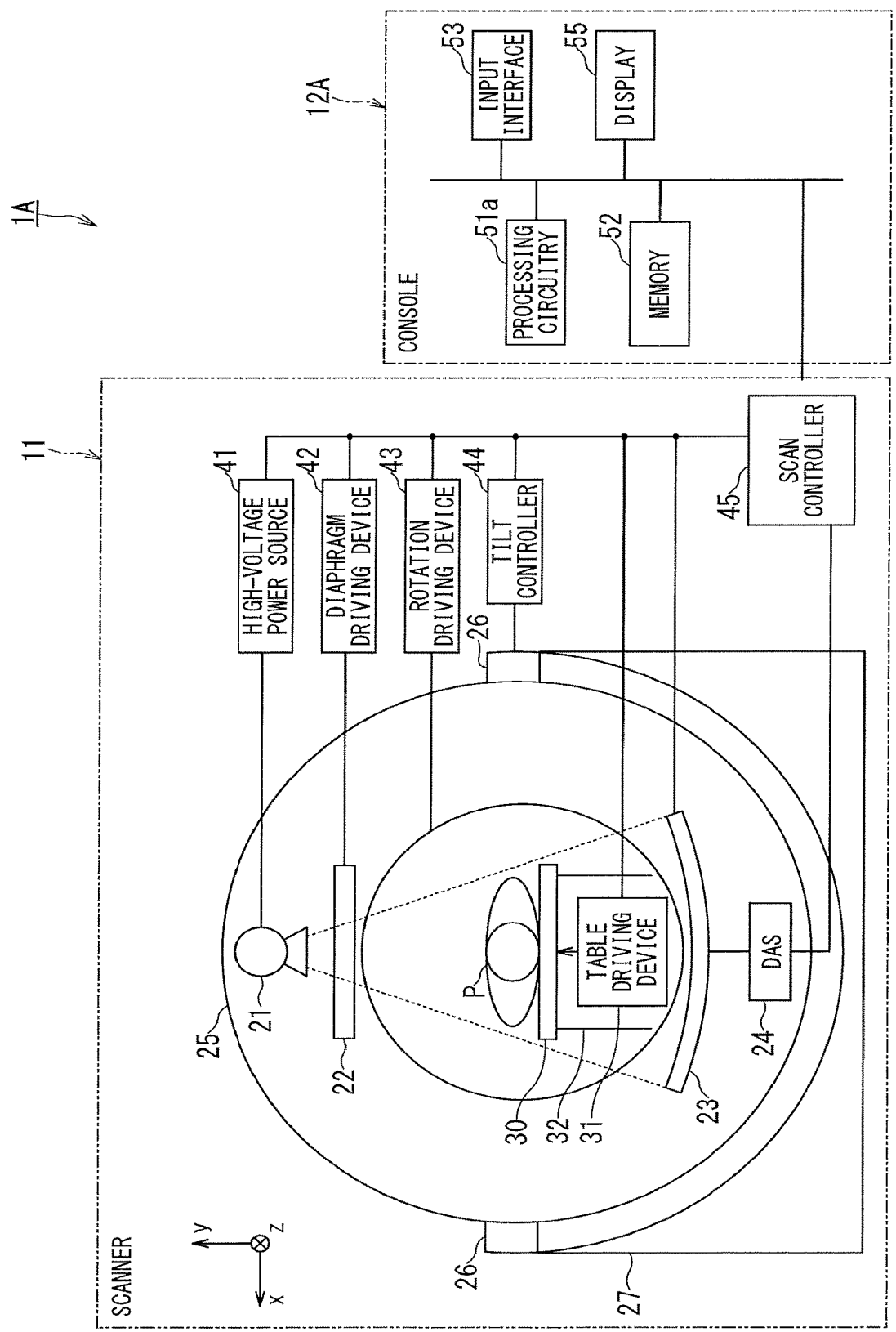
FIG. 1 is a general block diagram illustrating configuration of the X-ray CT apparatus 1A in the first embodiment.

Hereinafter, X-ray CT apparatuses of respective embodiments will be described by referring to the accompanying drawings.

In one embodiment, An X-ray CT apparatus includes: a rotating body and processing circuitry configured to extract an anatomical landmark from a medical image of an object acquired by a first scan, identify a shape of an anatomical site of the object based on the anatomical landmark, and set scanning conditions of a second scan based on the shape of the anatomical site, the second scan including a tilt scan in which a scan is performed under a condition where the rotating body is tilted, the scanning conditions including at least a tilt angle of the tilt scan.

Prior to description of embodiments of the present invention, viewpoints of the present inventors will be described.

Since an imaging range is different depending on gender and/or a body type of an object, it is preferable that an imaging range is appropriately set for each object. A conventional method of setting imaging conditions uses various types of template images in which each anatomical landmark (hereinafter, shortly referred to as an AL) stored in a database is extracted.

In each template image, an imaging range is defined in accordance with an anatomical site. Thus, it is possible to determine an imaging range of an object by performing coordinate transformation on the imaging range defined in the template image on the basis of ALs extracted from the scanogram image and ALs of the template image.

An X-ray CT apparatus can image an object under any of various scan modes such as a helical scan and a rotational scan. For instance, a variable helical pitch scan (hereinafter, referred to as a vHP scan) is known as one of scan modes of an X-ray CT apparatus. In a vHP scan, a wide range is imaged while imaging conditions are being switched for each of predetermined imaging ranges.

In the case of imaging the whole body under a vHP scan, an electrocardiographic synchronous scan is performed on the imaging range which includes the heart. In an electrocardiographic synchronous scan, e.g., imaging conditions are set in such a manner that projection data are acquired at a cardiac time phase at which influence of a heart beat is small in one cycle of a heartbeat. In other words, projection data of a predetermined cardiac time phase necessary for image reconstruction are acquired over plural heartbeats. Thus, in an imaging range including the heart in a vHP scan, table moving velocity is set at slower velocity as compared with other imaging ranges which do not include the heart.

When table moving velocity is slower, a time span during which an object is exposed to X-ray irradiation is longer and thus X-ray exposure to the object is increased. However, when the table is moved beyond the X-ray beam-width in the slice direction in one cycle of a heartbeat, the cardiac CT image to be reconstructed includes a missing part in the z-axis direction.

For the above reasons, the present inventors have worked out innovative configuration in which an imaging range is automatically set as narrowly as possible within a range where satisfactory image quality is maintained in terms of diagnosis. According to this configuration, it is possible to reduce total exposure dose in the entire imaging by minimizing an imaging range exposed to a large dose of X-rays under a condition where satisfactory image quality is maintained for a CT image to be acquired.

Hereinafter, a description will be given of embodiments of X-ray CT apparatuses equipped with the configuration of setting an imaging range in the above-described manner.

First Embodiment (1) Configuration

FIG. 1 is a general block diagram illustrating configuration of the X-ray CT apparatus 1A in the first embodiment. The X-ray CT apparatus 1A shown in FIG. 1 includes a scanner 11 and a console 12A.

The scanner 11 is installed in an examination room, and acquires projection data of an object P. The console 12A is installed in a control room which is adjacent to the examination room, and generates a CT image by reconstructing projection data inputted from the scanner 11.

The scanner 11 includes a rotating body 25, a table driving device 31, a high-voltage power source 41, a diaphragm driving device 42, a rotation driving device 43, a tilt controller 44, and a scan controller 45.

The rotating body 25 is a frame (i.e., housing) configured to rotatably support an X-ray tube 21, an X-ray detector 23, and a non-illustrated cooler described below, and is fixed to a base 27 with a non-illustrated fixed base. Under the control of the scan controller 45, the rotation driving device 43 causes the rotating body 25 to rotate about a rotational axis which is in parallel with the z-axis of the apparatus coordinate system.

As an example here, the x-axis, the y-axis, and the z-axis of the apparatus coordinate system is defined as follows: the vertical direction is defined as the y-axis direction; the z-axis is defined as the direction which is perpendicular to the y-axis and in parallel with the horizontal moving direction (i.e., the longitudinal direction) of the table; and the x-axis is defined as the direction which is perpendicular to both of the y-axis and the z-axis. In the present embodiment, it is assumed that the object P is placed on the table such that its body-axis direction matches the z-axis direction, unless otherwise specifically noted.

The rotating body 25 and the fixed base are tilted in the z-axis direction of the apparatus coordinate system by a tilt mechanism 26 which is provided between the fixed base and the base 27. The tilt mechanism 26 is equipped with a non-illustrated tilt bearing. The rotating body 25 and the fixed base integrally rotate about the tilt bearing. The tilt mechanism 26 tilts the rotating body 25 in accordance with a control signal inputted from the tilt controller 44 under the control of the scan controller 45. Details of a tilt operation of the rotating body 25 will be described below with reference to FIG. 2.

The rotating body 25 includes an opening section. The table driving device 31 moves the table 30 with the object P placed thereon into the opening section of the rotating body 25 at the time of imaging, and moves the table 30 to outside of the opening section after completion of imaging. As an example here, the negative direction of the z-axis is defined as the moving direction of the table 30 from outside of the opening section into inside of the opening section. In other words, the positive direction of the z-axis is defined as the moving direction of the table 30 from inside of the opening section into outside of the opening section. A supporting platform 32 is installed on the floor surface so as to support the table 30.

The table driving device 31 includes a non-illustrated table moving motor and a table moving mechanism. The table driving device 31 moves the table 30 upward and downward along the y-axis direction and horizontally moves the table 30 in the z-axis direction under the control of the scan controller 45.

The table moving mechanism is configured of, e.g., a rack and pinion mechanism. The table 30 moves along the rack meshing with the pinion (gear) by torque of the pinion which is generated by the table moving motor. Additionally, the table driving device 31 includes a non-illustrated stepping motor, and transmits position control information such as the current position of the table 30 and moving amount of the table 30 detected by the stepping motor to the scan controller 45.

The rotating body 25 includes an X-ray tube 21, an X-ray optical system 22, an X-ray detector 23, and a DAS (Data Acquisition System) 24.

The X-ray tube 21 generates an electron beam from its cathode in accordance with tube voltage supplied from the high-voltage power source 41, and generates X-rays by bombarding a metal target (i.e., its anode) with the electron beam. The X-rays generated by the X-ray tube 21 are radiated toward the X-ray detector 23. The X-ray tube 21 is supplied with electric power necessary for X-ray radiation under the control of the scan controller 45.

The X-ray optical system 22 controls an irradiation range of X-rays to be radiated onto the object P on the basis of a control signal from the diaphragm driving device 42 under the control of the scan controller 45. The X-ray optical system 22 is equipped with various types of control devices configured to control irradiation conditions such as dose of an X-ray beam, an irradiation range, a shape of an X-ray beam, and radiation quality. Specifically, the X-ray optical system 22 is equipped with, e.g., a wedge filter and a collimator. The wedge filter is a filter which is in the form of a convex-lens and formed of lightweight metal such as aluminum, and adjusts dose of X-rays generated by the X-ray tube 21. The collimator is a slit for narrowing down an irradiation range of X-rays, dose of which has been controlled and adjusted by the wedge filter.

The X-ray detector 23 is, e.g., a one-dimensional type detector in which detection elements are arrayed in plural rows in the channel direction and in one column in the slice direction. Note that the slice direction is perpendicular to the channel direction. As an example here, the slice direction is the direction of the rotational axis of the rotating body 25, and matches the z-axis direction under the condition where the rotating body 25 is not tilted, i.e., the tilt angle described below is zero degree. Additionally, the channel direction matches the x-axis direction regardless of the tilt state of the rotating body 25.

As another example of the X-ray detector 23, the X-ray detector 23 may be a two-dimensional array type detector in which many detection elements are arrayed in a matrix along the x-axis direction (i.e., the channel direction) and the slice direction. The X-ray detector 23 detects X-rays radiated from the X-ray tube 21.

A two-dimensional array type detector is also referred to as a multi-slice type detector. When the X-ray detector 23 is a multi-slice type detector, it is possible to scan a three-dimensional region having width in the slice direction by rotating the rotating body 25 by 360 degrees or by 180 plus α degrees.

The DAS 24 includes a non-illustrated amplifier and an A/D (Analogue/Digital) converter, amplifies signals of transmission data of X-rays detected by the respective detection elements of the X-ray detector 23, and converts the amplified transmission data into digital signals. The DAS 24 transmits projection data, which are generated on the basis of the transmission data detected by the X-ray detector 23, to the scan controller 45 via a non-illustrated data transfer device.

The console 12A of the X-ray CT apparatus 1A is configured on the basis of a computer, and can intercommunicate with an external device via a network such as a LAN (Local Area Network). The console 12A is configured of hardware such as processing circuitry 51a, a memory 52, an input interface 53, and a display 55.

The processing circuitry 51a is interconnected with the respective hardware components constituting the console 12A via a bus as a transmission path of common signals. Incidentally, the console 12 is equipped with a memory-medium drive in some cases.

The processing circuitry 51a may be configured of a special-purpose hardware or be configured to implement various types of functions by software processing of its built-in processor. As an example here, a description will be given of a case where the processing circuitry 51a implements various types of functions by software processing of its processor.

The above-described term "processor" means, e.g., a circuit such as a special-purpose or general-purpose CPU, a special-purpose or general-purpose graphics processing unit (GPU), an application specific integrated circuit (ASIC), a programmable logic device, and a field programmable gate array (FPGA). The above-described programmable logic device includes, e.g., a simple programmable logic device (SPLD) and a complex programmable logic device (CPLD). The processing circuitry 51a implements various types of functions by reading out programs stored in the memory 52 and executing the programs. Additionally or alternatively, the processing circuitry 51a implements various types of functions by reading out programs stored in its own processor and executing the programs.

Further, the processing circuitry 51a may be configured of a single processor or may be configured of a combination of plural processors which are independent of each other. In the latter case, plural memories 52 may be provided for the respective processors so that programs executed by each processor are stored in the memory 52 corresponding to this processor. As a further modification, one memory 52 may collectively store all the programs corresponding to the respective functions of the plural processors. The memory 52 is a memory medium including an external memory device such as a HDD (Hard Disk Drive) and an optical disc device in addition to a RAM (Random Access Memory) and a ROM (Read Only Memory). The memory 52 stores image data, data necessary for executing programs, and various types of programs executed by the processing circuitry 51a (including an application program and an operating system). Additionally, the memory 52 may store a program for controlling the operating system. Further, the memory 52 may store a program of a GUI (Graphical User Interface) which assists input from the input interface 53.

The input interface 53 is configured of input devices such as a keyboard, a mouse, a joystick, and a trackball. The input interface 53 receives input from a user via the input devices. When at least one input device is operated by an operator, the input interface 53 generates an input signal depending on this operation and outputs this input signal to the processing circuitry 51a.

The display 55 is a display device such as a liquid crystal display panel, a plasma display panel, and an organic EL (Electro Luminescence) panel. The display 55 displays imaging conditions and images such as a scanogram image under the control of the processing circuitry 51a.

Figure 2:
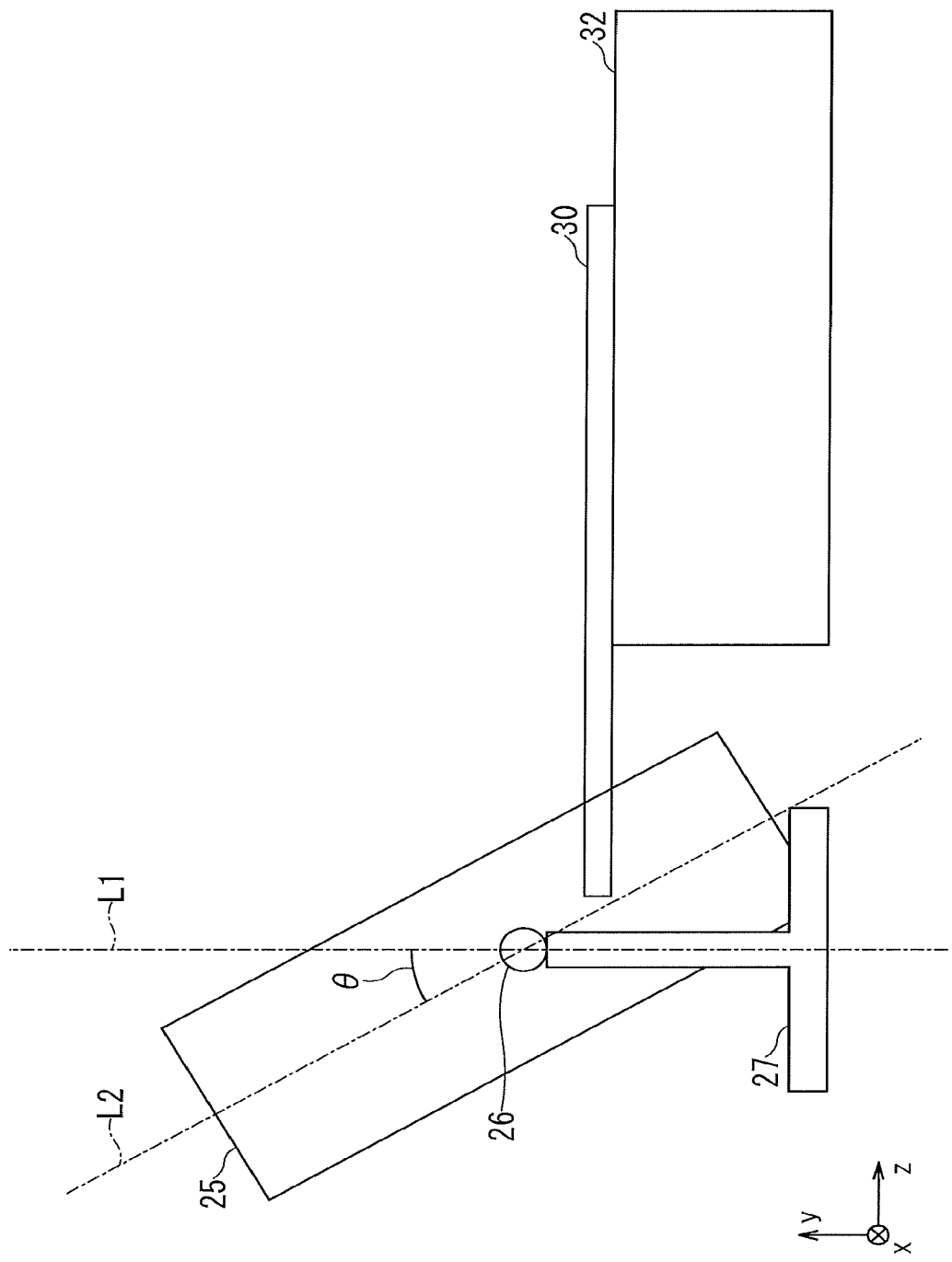
FIG. 2 is a schematic side view of the X-ray CT apparatus 1A of the first embodiment for describing the tilt mechanism.

FIG. 2 is a schematic side view of the X-ray CT apparatus 1A of the first embodiment for describing the tilt mechanism. FIG. 2 is a side view of the scanner 11 viewed from the x-axis direction under the state that the rotating body 25 is tilted. The chain line L1 in FIG. 2 is a straight line which is in parallel with the y-axis and passes through the center of the tilt mechanism 26. The chain line L2 is a straight line on the y-z plane and passes through the center of the tilt mechanism 26. A tilt angle θ is defined as the angle between the chain line L1 and the chain line L2.

Although a description has been given of the case where the rotating body 25 is tilted in the negative direction along the z-axis (i.e., backward tilting) in FIG. 2, the rotating body 25 is tiled in the positive direction along the z-axis (i.e., forward tilting) in some cases. When the backward tilting is defined as the positive tilt direction and the forward tilting is defined as the negative tilt direction, the rotating body 25 is tilted in the positive or negative tilt direction within a predetermined angle range such that the reference angular position of the rotating body 25 is tilt angle 0 degree at which the chain line L2 matches the chain line L1.

Figure 3:
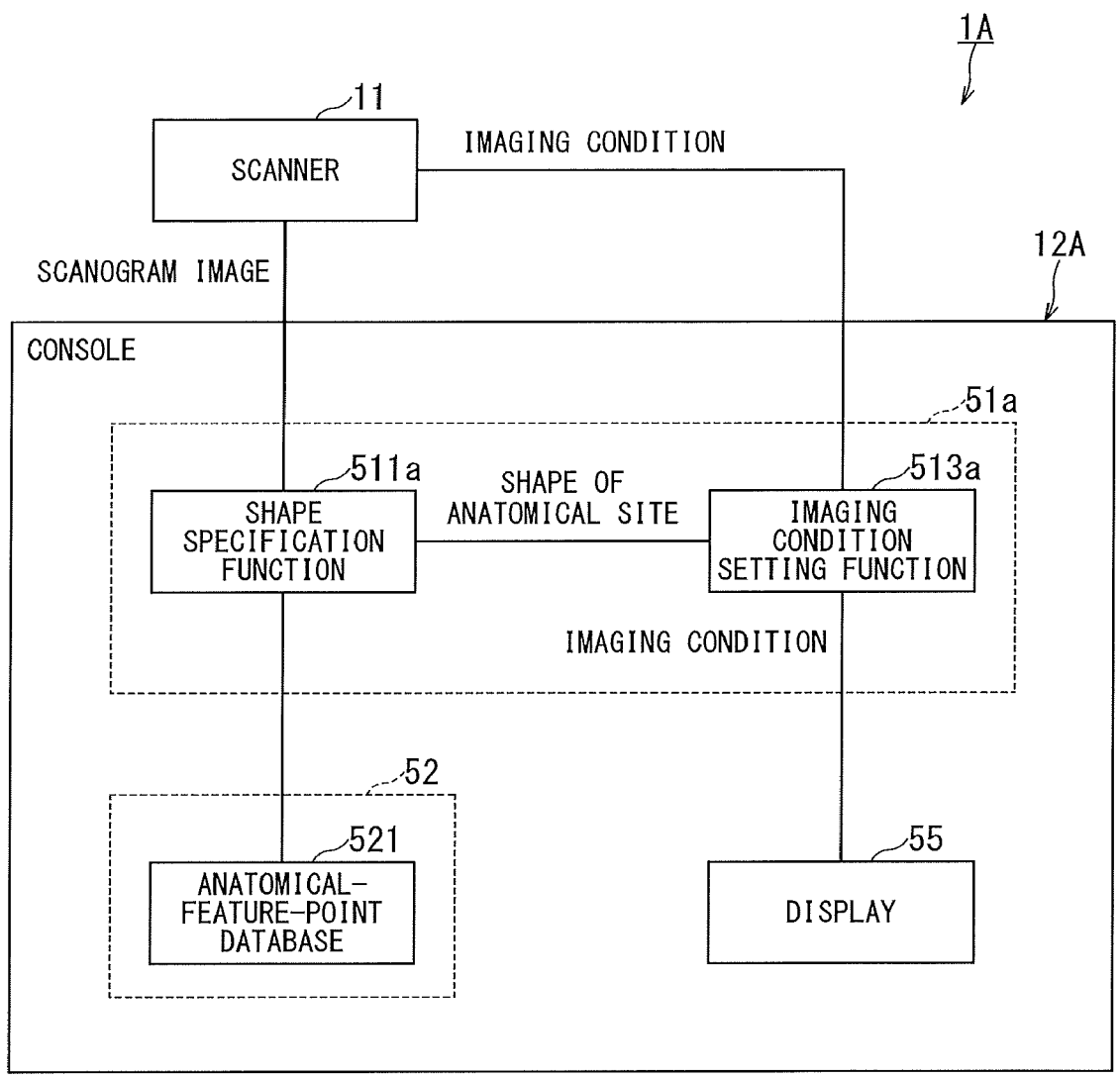
FIG. 3 is a block diagram illustrating functional configuration of the X-ray CT apparatus 1A in the first embodiment.

FIG. 3 is a block diagram illustrating functional configuration of the X-ray CT apparatus 1A in the first embodiment.

As shown in FIG. 3, the processing circuitry 51a of the console 12A implements a shape specification function 511a and an imaging condition setting function 513a. Each of the shape specification function 511a and the imaging condition setting function 513a is a function which the processor of the processing circuitry 51a implements by executing the corresponding program stored in the memory 52.

The shape specification function 511a extracts ALs from each scanogram image acquired by the scanner 11, and specifies a shape of each anatomical site included in each scanogram image on the basis of the extracted ALs.

ALs are extracted from a medical image on the basis of, e.g., model data which are generated by pattern recognition technology and/or machine learning. Model data are matching data used for associating respective ALs with feature points extracted from a medical image, from which ALs have not been extracted. In the above processing of associating respective ALs with feature points, image processing technology such as pattern recognition is used. Model data are determined by, e.g., machine learning and/or a mathematical statistics method with the use of correct answer data and feature points which are extracted from various image data acquired from objects including various ages, both genders, and various body shapes. Note that the above-described correct answer data are data of which ALs are determined on the basis of preliminarily acquired correct feature points.

ALs extracted from a medical image in the above-described manner include anatomical site information such as name of an organ and/or bone identified from the ALs and ID (Identification Data) which unambiguously or uniquely specifies the ALs. Additionally, there are plural ALs in each of anatomical sites such as an organ and a bone. Further, ALs include anatomical positional information in which the position of the tip and/or the center of this anatomical site is indicated by a patient coordinate system, for instance.

The shape specification function 511a specifies a shape of each anatomical site included in each scanogram image on the basis of anatomical site information and anatomical positional information both of which are included in ALs. As to the method of specifying a shape of each anatomical site to be performed by the shape specification function 511a, it will be described below in detail by referring to FIG. 5.

The imaging condition setting function 513a sets imaging conditions such as a tilt angle and an imaging range on the basis of a shape of each anatomical site. As to the method of setting a tilt angle and an imaging range, it will be described below in detail by referring to FIG. 6 to FIG. 8.

The scanner 11 performs a main scan based on imaging conditions determined by the imaging condition setting function 513a so as to acquire projection data of medical images for image diagnosis.

The memory 52 of the console 12A includes an anatomical-feature-point database 521. The anatomical-feature-point database 521 previously stores model data and algorithm necessary for extracting ALs from a CT image or a scanogram image acquired by the X-ray CT apparatus 1A. The above-described "previously" means to be in advance of imaging for generating medical images, and is, e.g., at the time of installation and adjustment of the X-ray CT apparatus 1A.

(2) Operation

Figure 4:
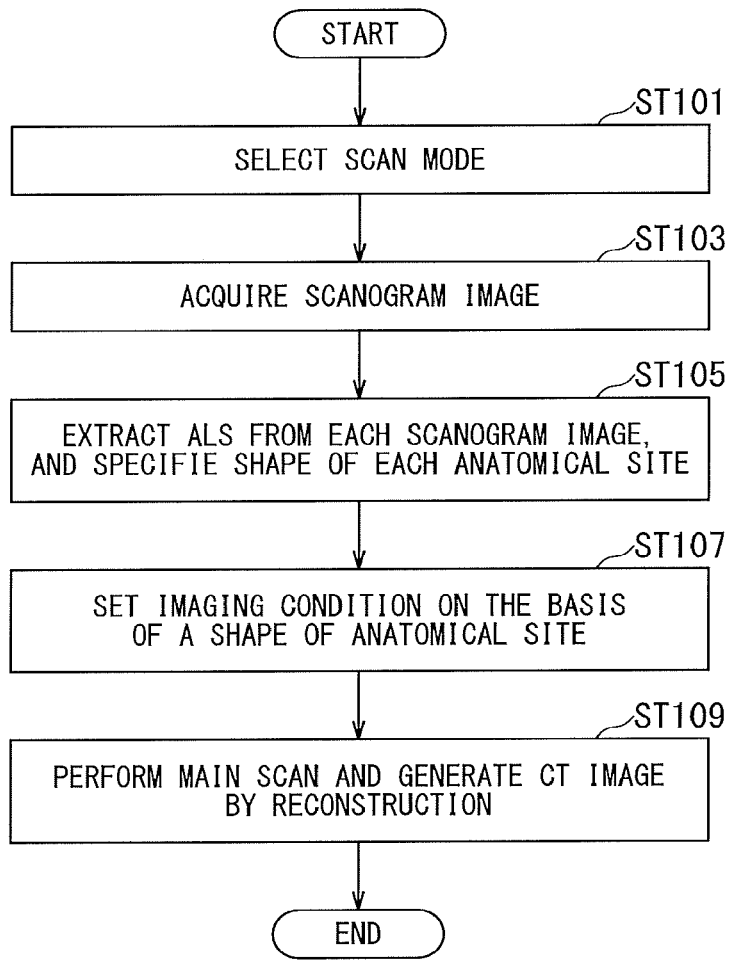
FIG. 4 is a flowchart illustrating an operation of the X-ray CT apparatus 1A in the first embodiment.

FIG. 4 is a flowchart illustrating an operation of the X-ray CT apparatus 1A in the first embodiment. Hereinafter, the operation of the X-ray CT apparatus 1A in the first embodiment will be described according to the step number in the flowchart of FIG. 4 by referring to FIG. 5 as required.

In the step ST101, a user selects a scan mode of a main scan. A timing of selecting a scan mode may be any time before setting imaging conditions of the main scan. Hereinafter, a description will be given of a case where a vHP scan is selected as a scan mode of the main scan.

In the next step ST103, the scanner 11 acquires projection data of one or plural scanogram images. Projection data of each scanogram image are acquired by moving the table 30 under the condition where the X-ray tube 21 and the X-ray detector 23 are fixed. For instance, the scanner 11 may apply a method called dual scanogram imaging to acquisition of scanogram images. In dual scanogram imaging, scanogram images are acquired in both of the y-axis direction (90 degrees) and the x-axis direction (0 degree).

Further, the scanner 11 may acquire a three-dimensional scanogram image by applying a scan method for a scanogram image which is called helical scanogram imaging. In helical scanogram imaging, the X-ray tube 21 and the X-ray detector 23 are integrally rotated about the object P while the table 30 is being moved.

In the next step ST105, the shape specification function 511a extracts ALs from each scanogram image, and specifies a shape of each anatomical site. Hereinafter, a description will be given of a method of specifying an anatomical shape from a three-dimensional scanogram image.

Figure 5:
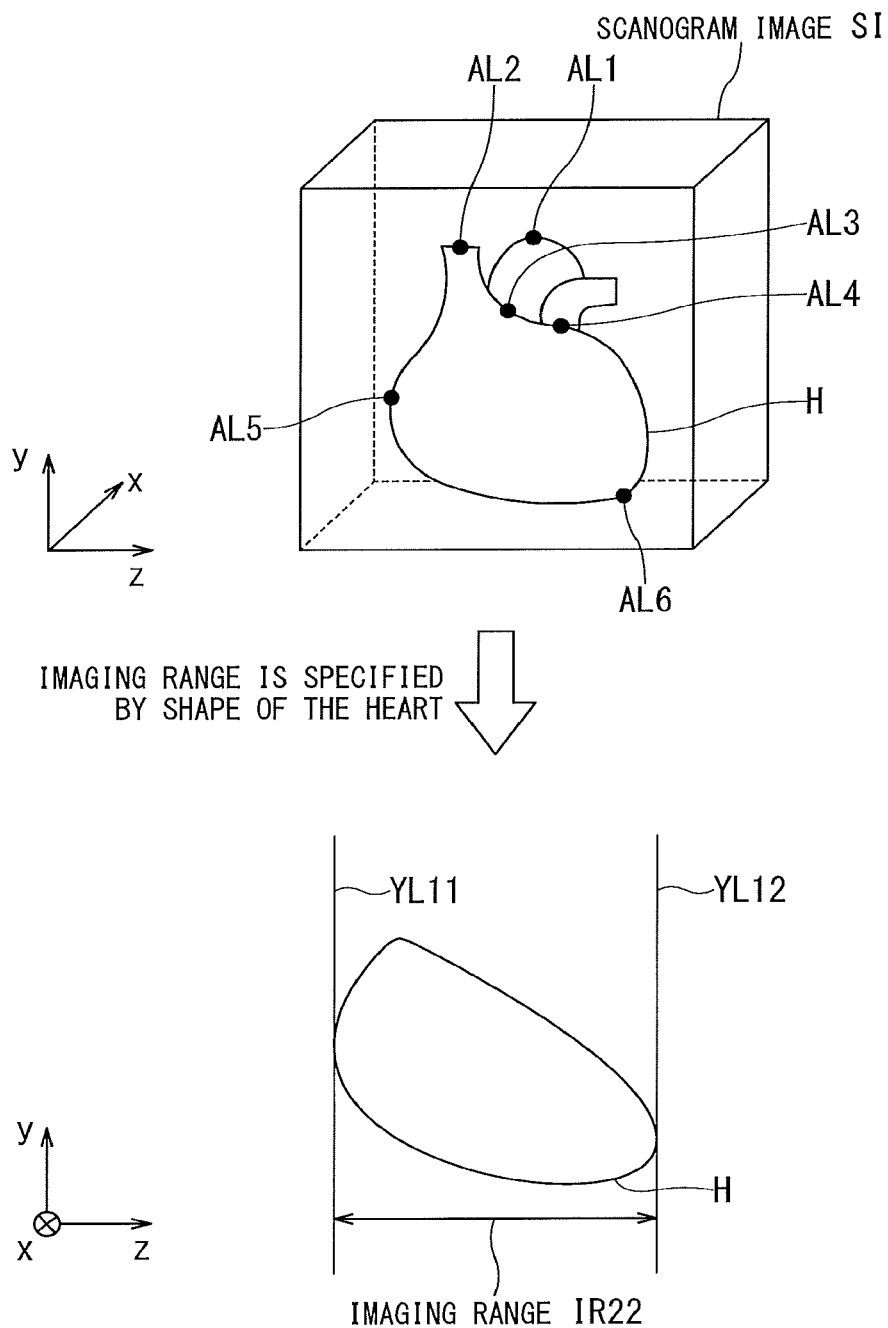
FIG. 5 is a schematic diagram illustrating a method of specifying a shape of an anatomical site in the first embodiment.

FIG. 5 is a schematic diagram illustrating a method of specifying a shape of an anatomical site in the first embodiment. The upper part of FIG. 5 shows a region including the heart H in a three-dimensional scanogram image which depicts the whole body of the object P. The upper part of FIG. 5 shows a case where six ALs including AL1 to AL6 are extracted for the heart H in the three-dimensional scanogram image SI. The lower part of FIG. 5 is a plan view when the shape of the heart H is viewed from the x-axis direction.

As shown in the upper part of FIG. 5, plural ALs are extracted from one anatomical site. ALs include anatomical positional information indicated by the patient coordinate system, and also include anatomical site information such as an organ, a body part, and a body tissue to which those ALs belong. Thus, when ALs are extracted from a three-dimensional scanogram image acquired from the object P, respective regions of bones and organs are identified by the extracted ALs. In other words, a localized region including the heart H can be extracted from a three-dimensional scanogram image depicting the whole body, by using plural ALs which indicates the heart H.

When the region of the heart H is identified on a three-dimensional scanogram image, for instance, the contour of the heart H can be extracted by analyzing pixel values around the ALs under an image processing technique called segmentation. Plural AL are specified from the heart H, and it is possible to specify the detailed shape of the heart H by combining partial contours of the heart H extracted from peripheral regions of the respective ALs.

Note that it is possible to specify a shape of each anatomical site on the basis of ALs from a scanogram image and/or a dual scanogram image in a similar manner as described above.

Additionally, a method of specifying a shape of an organ is not limited to the above-described segmentation technique. Contour model data and/or surface shape model data may be preliminarily stored for each anatomical site in the anatomical-feature-point database 521 such that a contour and/or surface shape of each anatomical site is determined on the basis of, e.g., nonrigid registration.

In a vHP scan, the heart H is the only imaging target of an electrocardiographic synchronous scan, and thus it is possible to narrow an imaging range of the electrocardiographic synchronous scan by specifying the shape of the heart H. For instance, as shown in the lower part of FIG. 5, two straight lines YL11 and YL12 may by drawn so as to be in parallel with the y-axis and be in point contact with the exterior edge of the heart H so that the width between the straight lines YL11 and YL12 along the z-axis direction is set as the imaging range of the heart H. As described above, it is possible to minimize an imaging range including the entire heart H by determining the minimum width of the entire heart H along the z-axis direction and setting this minimum width as the imaging range. This algorithm minimizes the region outside the heart H in the entire imaging range on which the electrocardiographic synchronous scan is performed, and thus exposure dose can be reduced.

Returning to FIG. 4, a description of the flowchart is continued.

In the step ST107, the imaging condition setting function 513a sets imaging conditions on the basis of a shape of each anatomical site. For instance, the imaging condition setting function 513a sets imaging conditions such as an imaging range on the basis of the shape of the heart H specified by the shape specification function 511a.

In the next step ST109, the scanner 11 performs the main scan on the basis of the imaging conditions which are set by the imaging condition setting function 513a. The projection data acquired in the main scan are transmitted from the scanner 11 to the console 12A. The processing circuitry 51a of the console 12A generates one or plural CT images by reconstructing the projection data, and causes the display 55 to display the generated CT images.

The foregoing is the description of the flowchart. Hereinafter, a method of setting imaging conditions on the basis of a shape of the heart will be supplemented by referring to FIG. 6 and FIG. 7.

Figure 6:
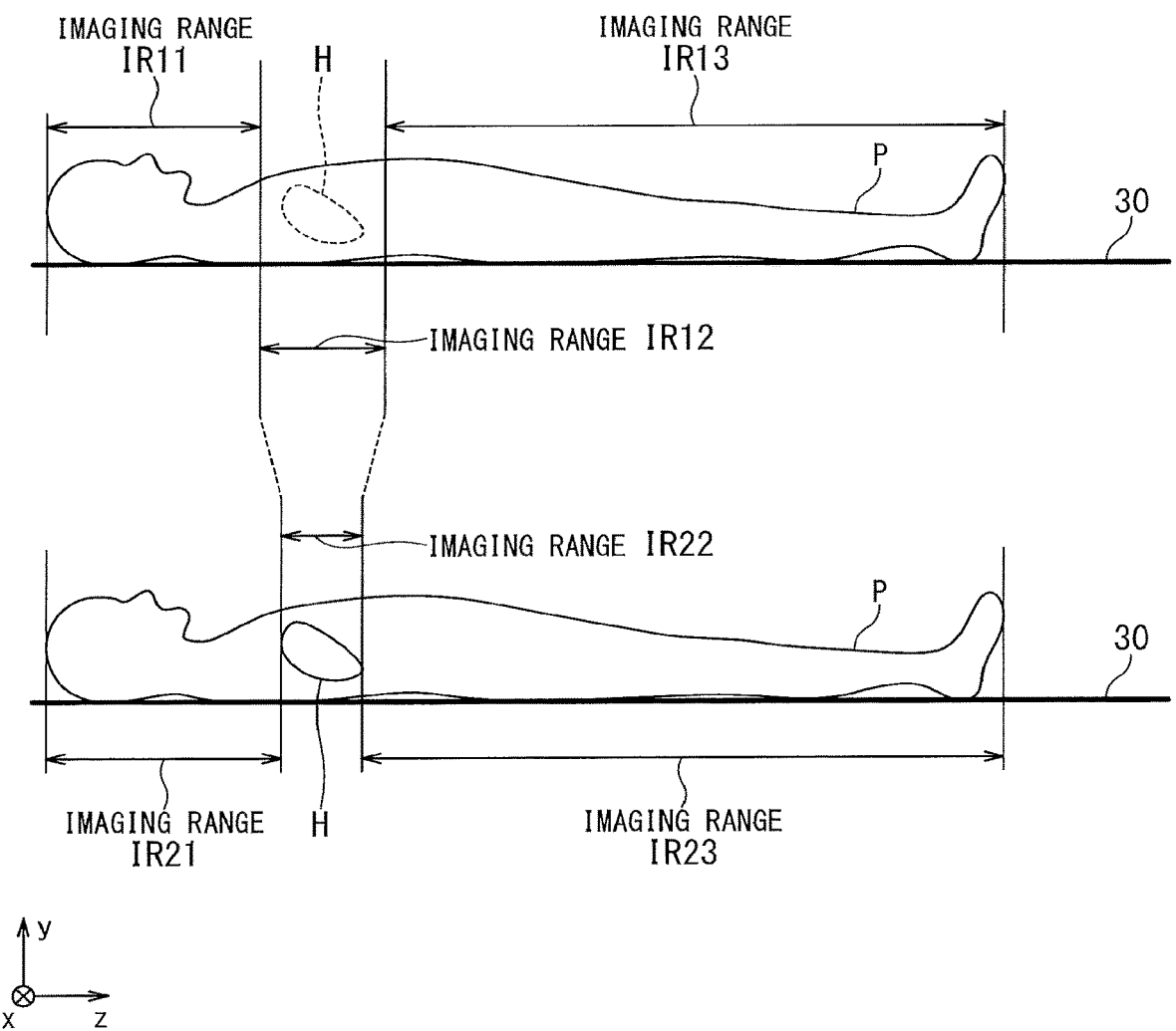
FIG. 6 is a schematic diagram illustrating an imaging range of a vHP scan in the first embodiment.

FIG. 6 is a schematic diagram illustrating an imaging range of a vHP scan in the first embodiment. The upper part of FIG. 6 indicates an imaging range in a vHP scan in conventional technology. Conversely, the lower part of FIG. 6 corresponds to the present embodiment and illustrates an imaging range which are set by the imaging condition setting function 513a on the basis of the shape of the heart H specified by the shape specification function 511a.

In conventional technology, the imaging range IR12 including the heart H is set under the state where the shape of the heart H is not specified. In the upperpart of FIG. 6, a region including the heart to be subjected to an electrocardiographic synchronous scan is indicated by the imaging range IR12, and the rest region is indicated by the imaging range IR11 and the imaging range IR13.

In the first embodiment, the imaging range IR22 is set by specifying the shape of the heart H on the basis of ALs. Thus, the imaging range IR22 shown in the lower part of FIG. 6 is narrower in width in the z-axis direction and smaller in volume than the imaging range IR12 in the upper part of FIG. 6. The imaging range IR21 and the imaging range IR23 are expanded by the volume decrement of the imaging range IR22.

In a vHP scan, the heart H is imaged by an electrocardiographic synchronous scan and exposure dose of an imaging range including the heart H is large. Since exposure dose is relatively large in an electrocardiographic synchronous scan in the entire imaging, it is possible to suppress total exposure dose in the entire imaging by limiting a range of an electrocardiographic synchronous scan to the heart H as shown in the lower part of FIG. 6.

Although a description has been given of the case where an imaging range is specified in accordance with the minimum width of the heart H in the z-axis direction in FIG. 6, a method of reducing exposure dose is not limited to the aspect of FIG. 6. For instance, it is possible to reduce exposure dose by tilting the rotating body 25 in accordance with the shape of the heart H and further narrowing the imaging range of the heart H.

Figure 7:
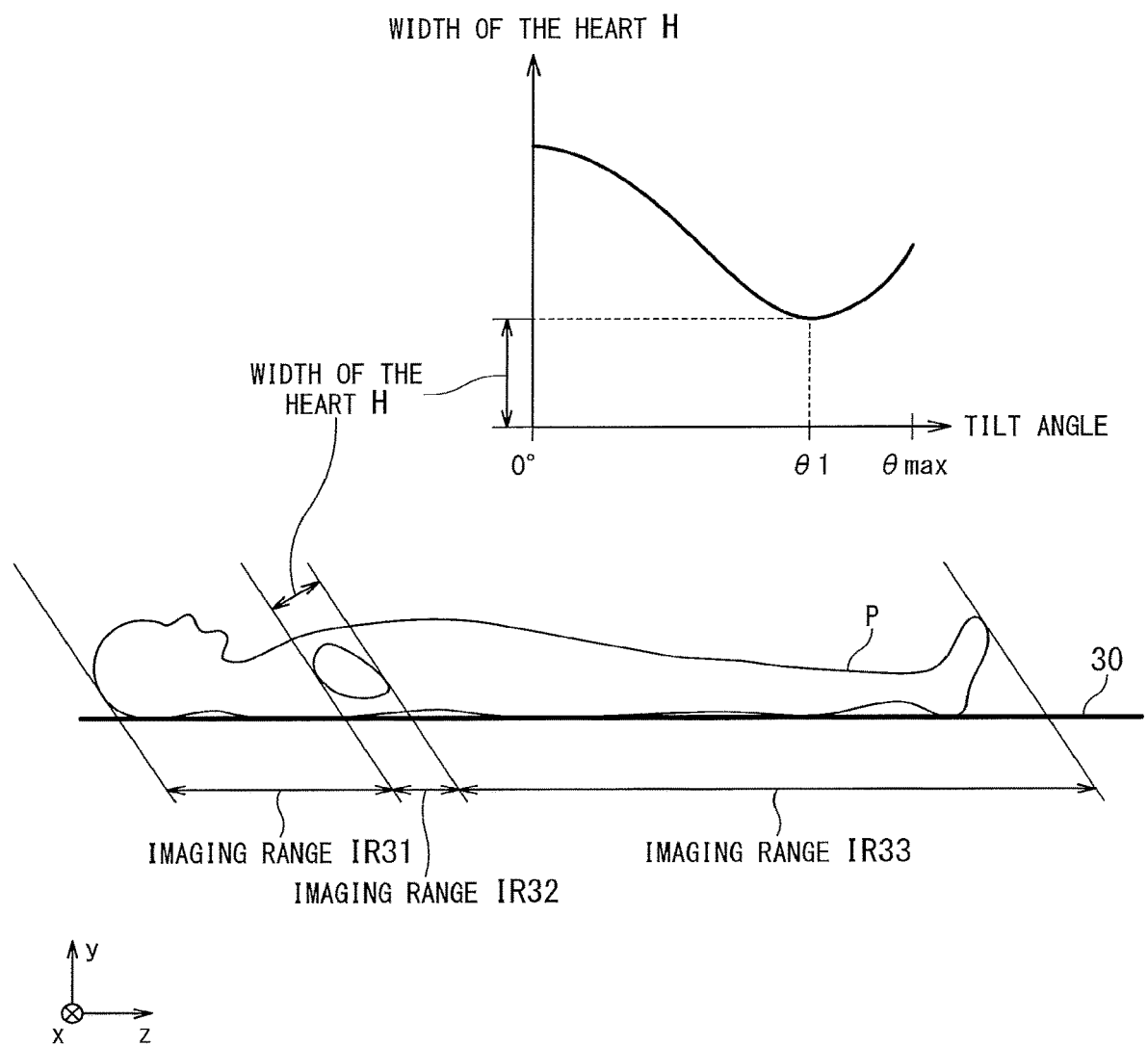
FIG. 7 is a schematic diagram illustrating a method of computing a tilt angle of a vHP scan in the first embodiment.

FIG. 7 is a schematic diagram illustrating a method of computing a tilt angle of a vHP scan in the first embodiment. The upper part of FIG. 7 is a graph indicating relationship between width of the heart H and a tilt angle. In the upper part of FIG. 7, the vertical axis indicates width of the heart H and the horizontal axis indicates a tilt angle. The rotating body 25 tilts in the positive or negative direction by a predetermined angle such that the reference angular position is the tilt angle 0 degree. The maximum tilt angle in the positive direction is indicated as θ max. The width of the heart H in FIG. 7 indicates the minimum width in which the entire heart H is contained in the X-ray irradiation range of the X-ray detector 23 in the slice direction. The lower part of FIG. 7 illustrates a case where the imaging range IR32 is set on the basis of the width of the heart H determined from the graph of FIG. 7.

When the shape of the heart H is approximately regarded as an ellipse, the short axis of this ellipse is not in parallel with the z-axis of the apparatus coordinate system. When X-rays are radiated without tilting the rotating body 25, the slice direction of the X-ray detector 23 matches the z-axis direction. Thus, as compared with a case where the rotating body 25 is not tilted, the imaging range of the heart H can be set as a narrower range by tilting the rotating body 25 in the positive direction such that the slice direction of the X-ray detector 23 matches the short axis direction of the heart H approximately regarded as an ellipse.

As the rotating body 25 is tilted in the positive direction, the minimum width including the entire heart H changes depending on a tilt angle as shown in the graph of FIG. 7. In other words, the larger the tilt angle becomes in the positive direction from 0 degree, the narrower the minimum width including the entire heart H becomes. At the tilt angle θ1, the minimum width including the heart H takes the smallest value. In other words, the slice direction of the X-ray detector 23 matches the short axis direction of the heart H at the tilt angle θ1. The larger the tilt angle becomes in the positive direction from θ1, the wider the minimum width including the entire heart H gradually becomes. As described above, on the basis of the shape of the heart H, the imaging condition setting function 513a computes the tilt angle by which the imaging range including the entire heart H is minimized.

When the rotating body 25 is tilted, X-ray transmission length inside the object becomes larger than a case where the rotating body 25 is not tilted. In the following description, a straight line inside the object along which X-rays passes is referred to as a path. Length of a path in the case of tilting the rotating body 25 is larger than a case where the rotating body 25 is not tilted. Length of a path is in proportional to exposure dose. The longer a path is, the larger exposure dose becomes.

For those reasons, the respective components of the X-ray CT apparatus 1A may be configured to provisionally change imaging conditions including length of a path, a tilt angle, an imaging range, and number of scans and to finally select such imaging conditions that the total exposure dose is minimized. The above-described number of scans means number of rotational scans. When a desired range cannot be imaged by one rotational scan, this desired range is imaged by combining plural rotational scans in some cases in such a manner that imaging ranges of the respective rotational scans partially overlap each other.

The total exposure dose in imaging is, e.g., measured or evaluated by DLP (Dose Length Product). DLP is a value obtained by multiplying width of an object in the body axis direction to be imaged in one examination by dosage index called CDTI (Computed Tomography Dose Index). CDTI is specified by a dose profile in the body axis direction in one rotational scan. A dose profile is, e.g., such a graph of absorbed dose of X-ray passing through a human body in one rotational scan that beam width in the body axis direction of the human body and a position in the body axis direction are used as parameters.

The total exposure dose to an object in a main scan can be computed from a scanogram image and imaging conditions. For instance, the imaging condition setting function 513*a* determines imaging conditions by which total exposure dose is minimized, on the basis of imaging conditions such as X-ray absorption rate specified from a scanogram image, X-ray irradiation dose, length of a path computed from a tilt angle and body thickness of an object, and an imaging range.

Incidentally, the X-ray CT apparatus 1A may be configured such that a prioritized condition can be selected from all the imaging conditions in processing of determining the imaging conditions by which total exposure dose is minimized. Additionally or alternatively, the X-ray CT apparatus 1A may set the imaging conditions by using different weighting coefficients for weighting the respective imaging conditions so that total exposure dose is minimized. For instance, when number of scans is set as a prioritized condition, the imaging condition setting function 513*a* determines such imaging conditions that total exposure dose is minimized and number of scans is minimized or low.

Although a description has been given of the case where an anatomical site is the heart and an imaging range is set for this anatomical site, in the case of another anatomical site except the heart such as the liver, it is possible to include the entirety of this anatomical site in the imaging range and minimize the imaging range in a similar manner as described above.

Additionally, though a description has been given of the case where a shape of an anatomical site is specified on the basis of ALs extracted from a scanogram image and an imaging range is set, an image to be used for specifying a shape of an anatomical site is not limited to a scanogram image. A shape of an anatomical site may be extracted from a medical image which have been acquired by a main scan. For instance, when plural main scans are sequentially performed, imaging conditions of the next main scan are sometimes set on the basis of medical images which have been acquired in the last (i.e., immediately previous) main scan. In this case, the X-ray CT apparatus 1A may be configured to specify a shape of an anatomical site from the medical image acquired in the previous main scan and set an imaging range of the next main scan in a similar manner as described above.

Additionally, an imaging condition to be switched in a vHP scan is not limited to table moving velocity.

A vHP scan is used for, e.g., a whole-body CT for multi-trauma patients which is for examining fracture and hemorrhage through the whole body. Image quality required for image diagnosis is different depending on each anatomical site such as the head and the abdomen. For instance, higher image quality is required for the head than the abdomen. However, in a helical scan, the whole body is imaged by the unified X-ray intensity. Since imaging conditions can be set for each anatomical site in a vHP scan such that a CT image having satisfactory image quality for diagnosis can be acquired for each anatomical site, a vHP scan is effective for imaging like a whole-body CT for multi-trauma patients.

Image quality in a CT image is determined by, e.g., a SD (Standard Deviation) value. A SD value in a CT image is an index indicative of dispersion of CT values. The smaller a SD value of a CT image is, the higher image quality of this CT image becomes because noise included in this CT image is smaller. A SD value is one of imaging conditions.

In the case of reducing noise of CT images, exposure dose is generally increased such that X-rays are radiated by higher X-ray intensity. Thus, when an SD value is small, X-ray intensity is large. Conversely, when an SD value is large, X-ray intensity is small. An SD value can be changed for each imaging range in a vHP scan. Thus, exposure dose of the entire imaging can be reduced by specifying a position and a shape of a target organ on the basis of ALs extracted from a scanogram image and then minimizing the imaging range, for which lower noise is required and thus large X-ray intensity is set, such that the entirety of the target organ is included in the imaging range in a similar manner as described above.

Although a description has been given of a vHP scan, a scan mode is not limited to a vHP scan. Hereinafter, a description will be given of a case where the technique of the first embodiment is applied to another scan mode by referring to FIG. 8 to FIG. 10.

Figure 8:
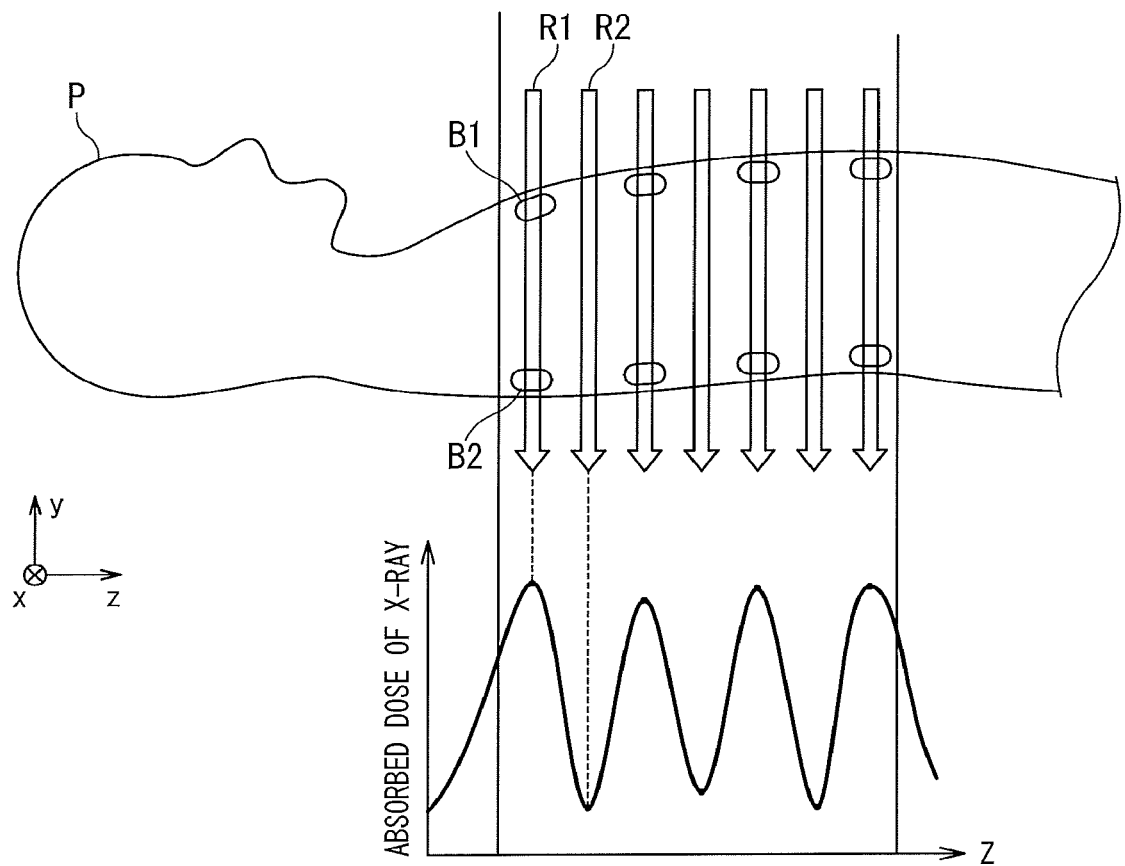
FIG. 8 is a schematic diagram illustrating X-ray absorption rate in imaging for the chest.
Figure 9:
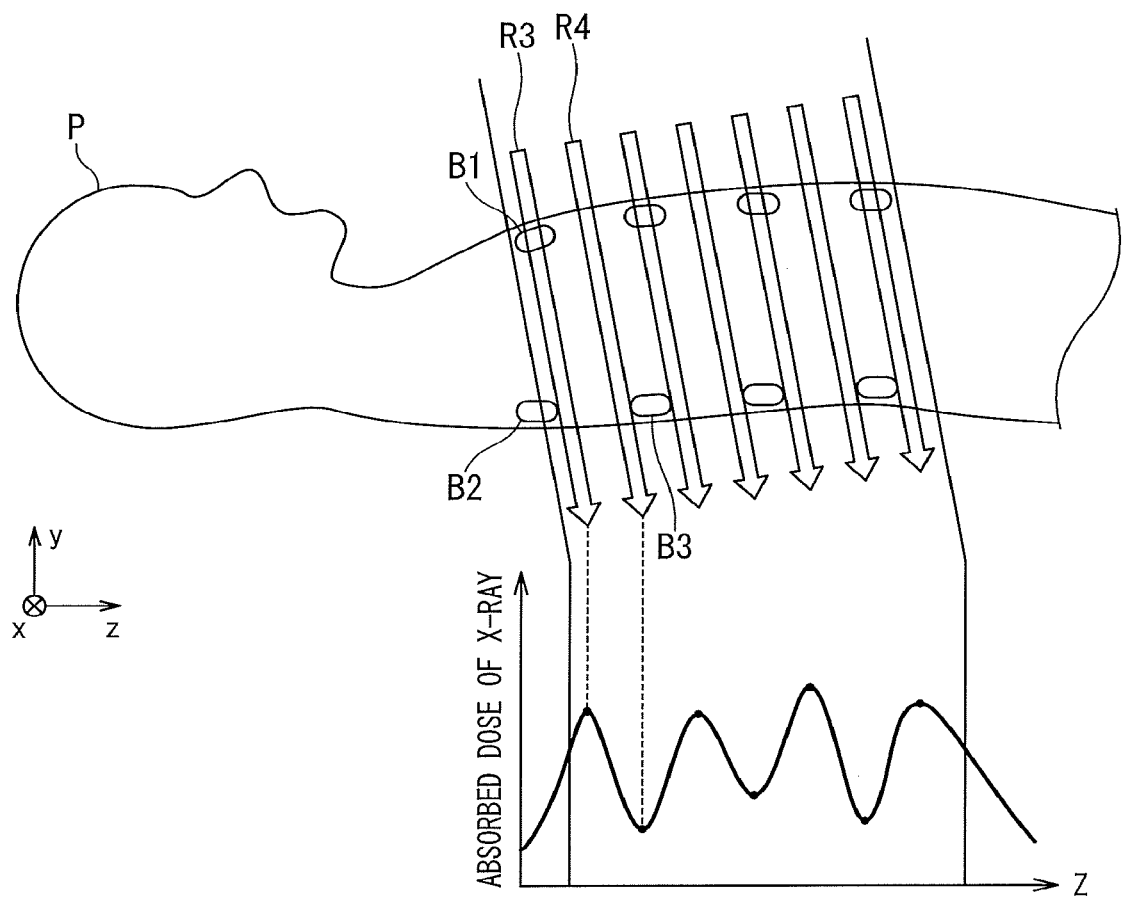
FIG. 9 is a schematic diagram illustrating X-ray absorption rate in imaging for the chest when the rotating body 25 is tilted.
Figure 10:
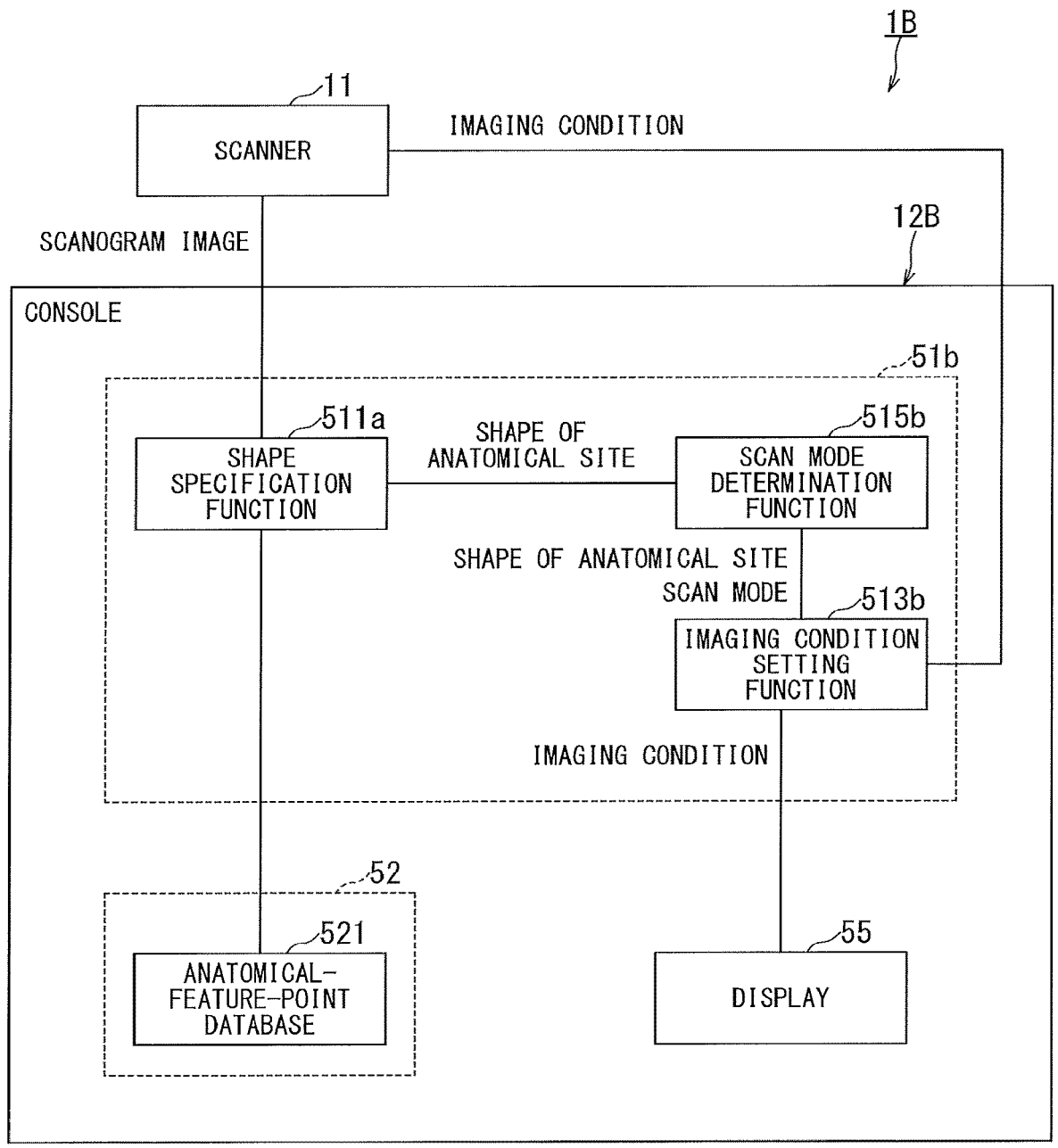
FIG. 10 is a functional block diagram illustrating the X-ray CT apparatus 1B of the second embodiment.

In FIG. 8 to FIG. 10, a description will be given of a case where the chest is imaged under a helical scan. The chest differs from other anatomical sites in that ribs exist on the body surface side of the object P. Ribs are bones which extend from the dorsal side to the abdominal side of a human body so as to cover the organs inside the chest such as the heart and the lungs. Additionally, when the object P is placed on the table 30 such that the body axis direction matches the z-axis direction, under the assumption that each rib is approximated by a C-shaped ring roughly in parallel with the x-y plane (i.e., axial plane), the extending plane of each rib is slightly tilted from the x-y plane and this tilt is indicated by a predetermined tilt within the y-z plane. Since a bone is a tissue with high X-ray absorption rate, in the case of imaging the chest, it is preferable to image each region including a rib with higher X-ray intensity than regions in which any part of a rib is not included.

FIG. 8 is a schematic diagram illustrating X-ray absorption rate in imaging for the chest. The upper part of FIG. 8 shows a sagittal cross-section of the object P onto which X-rays are radiated in the y-axis direction. The lower part of FIG. 8 is a graph indicating change of X-ray absorption rate in the z-axis direction.

As shown by the graph in the lower part of FIG. 8, the X-ray absorption rate of the region R1 which includes at least a part of the ribs B1 and B2 is higher than the X-ray absorption rate of the region R2 which does not include any part of a rib. The X-ray CT apparatus 1A adjusts X-ray intensity based on AEC (auto exposure control). AEC is, e.g., a technique of adjusting X-ray intensity of a main scan on the basis of X-ray absorption rate acquired from a scanogram image.

Since precision of setting an X-ray detection range has been improved by multi-row structure of an X-ray detector, in some cases, the region R1 including ribs and the region R2 where any part of a rib is not included are imaged, i.e., irradiated with X-rays at the same timing. In this case, X-ray intensity of the main scan is adjusted such that the region R1 with higher X-ray absorption rate is imaged with satisfactory image quality, and thus X-ray intensity of the chest imaging is sometimes set to a high value as a whole.

In the first embodiment, imaging conditions including a tilt angle are set on the basis of a shape of an anatomical site extracted from a scanogram image. Hence, it is possible to reduce X-ray dose by applying the technique of the first embodiment to the chest imaging under a helical scan shown in FIG. 8.

FIG. 9 is a schematic diagram illustrating X-ray absorption rate in imaging for the chest when the rotating body 25 is tilted. As shown in FIG. 9, the rib B2 on the dorsal side is excluded from the region R3 by tilting the rotating body 25, and X-ray absorption rate of the region R3 becomes lower than that of the region R1 in FIG. 8. The region R4 indicates a region where any part of a rib is not included like the region R2 in FIG. 8.

Out of all the imaging regions to be set for imaging the chest, some imaging regions inevitably includes at least a part of a rib like the region R3. However, by tilting the rotating body 25, a spatial outer border of each region which inevitably includes at least a part of a rib can be optimized such that this region includes lower volume of a rib (i.e., a part of a rib on the dorsal or abdominal side only). Thus, when a tilt angle is appropriately set, X-ray intensity can be set to a lower value as compared with a case where a tilt angle is not set as an imaging condition (e.g., a case where a tilt angle is uniformly set as 0 degree). When X-ray intensity can be set to a lower value, exposure dose of the entire imaging can be reduced.

For instance, the imaging condition setting function 513a may be configured to compute a tilt angle by which the maximum value of X-ray absorption rate becomes the lowest, on the basis of a scanogram image. Additionally, the imaging condition setting function 513a may be configured to compute how much an extending plane of each rib (approximated by a C-shaped ring) is inclined with respect to the x-y plane and to set a tilt angle based on the computed inclination of each rib.

Further, for instance, it is possible to compute interval between adjacent two ribs in the z-axis direction by using distance between ALs of adjacent two ribs on the dorsal or abdominal side. For instance, when a localized region in the chest is imaged, it is possible to suppress X-ray exposure dose by tilting the rotating body 25 such that each X-ray beam radiated from the X-ray source passes through an interval between adjacent two ribs.

Note that the X-ray CT apparatus 1A can adjust a shape of an X-ray beam and an X-ray irradiation range by controlling the X-ray optical system 22. In other words, width of an X-ray beam in the slice direction can be adjusted depending on interval between adjacent two ribs which is computed from ALs. Thus, on the basis of a shape of an anatomical site, it is possible to set imaging conditions by which X-rays do not pass through any rib. When imaging is performed by avoiding X-ray exposure to each rib, X-ray intensity can be lowered and thus exposure dose can be reduced.

Although a description has been given of the case where exposure dose is reduced by appropriately setting a tilt angle for an imaging region including a rib, an imaging condition used for reducing exposure dose is not limited to a tilt angle. For instance, the technique of the first embodiment can be applied to another anatomical site where respective position of a pair of organs are left-right asymmetric like kidneys or a position of a specific organ is deviated from the center line of the whole body like the pancreas. For instance, exposure dose can be reduced by setting a specific position of the table 30 as an imaging condition on the basis of ALs, in such a manner that the straight line passing through the respective centers of both kidneys becomes in parallel with the channel direction of the X-ray detector 23 at this specific position of the table 30.

As described above, the X-ray CT apparatus 1A of the first embodiment can narrow an imaging range which includes the entirety of the target anatomical site of the object P, on the basis of the shape of this anatomical site extracted from a scanogram image. Thus, exposure dose of the entire imaging can be reduced while satisfactory imaging quality required for image diagnosis is maintained. Additionally, since a tilt angle can be appropriately set on the basis of a shape of a target anatomical site of the object P, an imaging range including the entirety of the target anatomical site can be minimized and thus exposure dose can be further reduced.

Second Embodiment (1) Configuration

The X-ray CT apparatus 1B of the second embodiment includes a function of determining a scan mode on the basis of a shape of an anatomical site in addition to the respective functions of the X-ray CT apparatus 1A of the first embodiment. The X-ray CT apparatus 1B of the second embodiment slightly differs from the X-ray CT apparatus 1A of the first embodiment in terms of configuration. For this reason, as shown in FIG. 10, components of the X-ray CT apparatus 1B which are different from the first embodiment are assigned with reference signs different from the first embodiment.

FIG. 10 is a functional block diagram illustrating the X-ray CT apparatus 1B of the second embodiment. As shown in FIG. 10, processing circuitry 51b of a console 12B implements the shape specification function 511a, an imaging condition setting function 513b, and a scan mode determination function 515b. Each of the shape specification function 511a, the imaging condition setting function 513b, and the scan mode determination function 515b is a function which a processor of the processing circuitry 51b implements by executing the corresponding program stored in the memory 52.

The scan mode determination function 515b determines a scan mode based on a shape of an anatomical site specified by the shape specification function 511a. For instance, the scan mode determination function 515b determines which of a rotational scan or a plural-rotation scan is used as a scan mode, on the basis of a shape of an anatomical site.

A rotational scan is a scan mode in which imaging is completed by rotating the rotating body 25 by 360 degrees or by 180 degrees plus an irradiation angle of an X-ray beam.

Contrastively, a plural-rotation scan is a scan mode of moving the table 30 by a predetermined amount in the z-axis direction each time one rotational scan is completed. In other words, a plural-rotation scan is a scan mode in which a rotational scan and movement of the table 30 are repeated.

In a plural-rotation scan, one CT image is generated by combining plural CT images which are acquired in the respective rotational scans. Thus, since each scanning range is partially superimposed on the scanning range of the immediately previous scan and the scanning range of the next scan, exposure dose of a plural-rotation scan is higher than that of a rotational scan. The method of determining a scan mode will be described below in detail by referring to FIG. 12 and FIG. 13.

The imaging condition setting function 513b has a function of setting imaging conditions in accordance with the scan mode determined by the scan mode determination function 515b in addition to the function of the imaging condition setting function 513a in the first embodiment. The imaging condition setting function 513b computes a tilt angle of a rotational scan based on, e.g., a shape of an anatomical site.

(2) Operation

Figure 11:
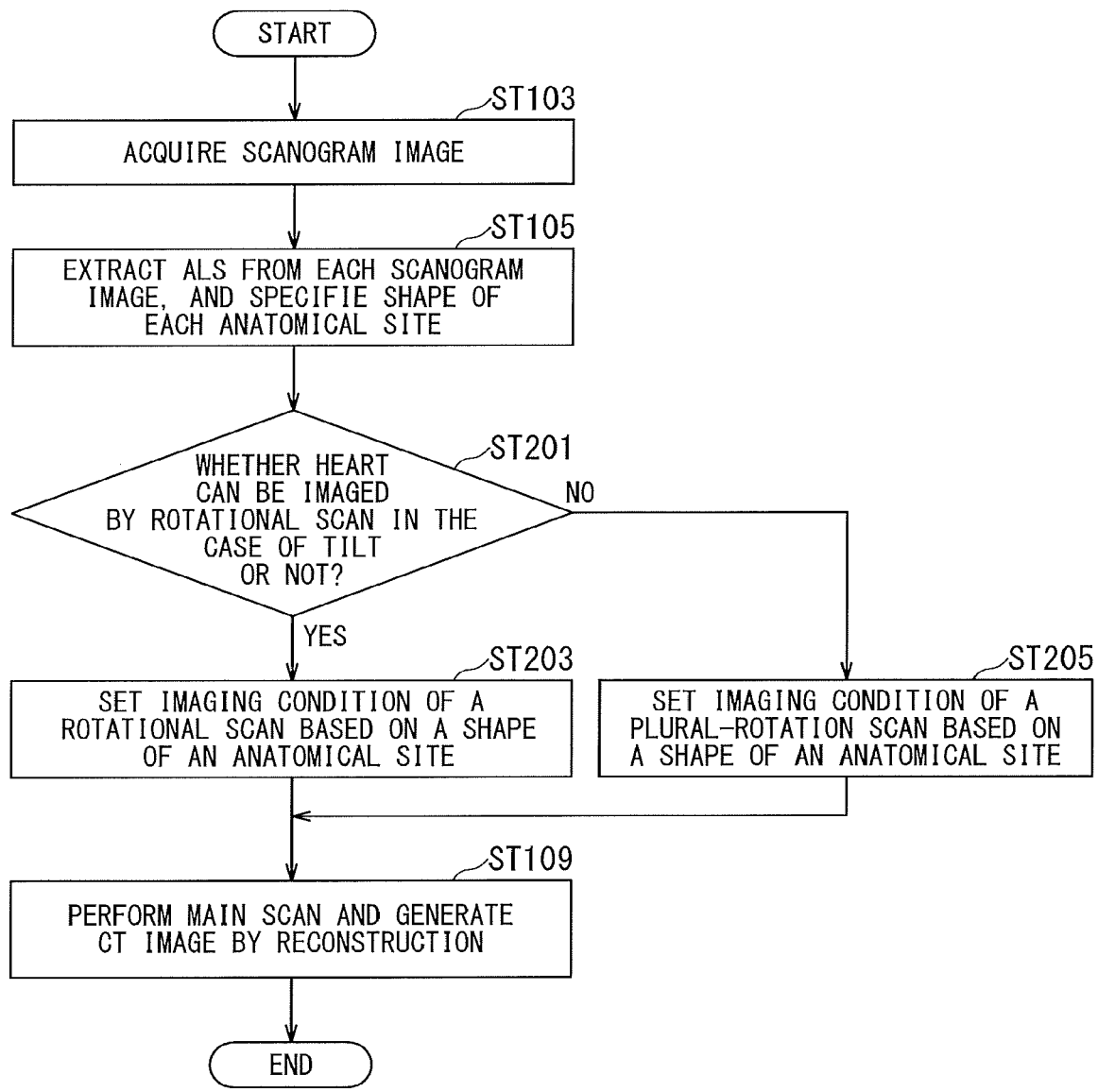
FIG. 11 is a flowchart illustrating an operation of the X-ray CT apparatus 1B of the second embodiment.

FIG. 11 is a flowchart illustrating an operation of the X-ray CT apparatus 1B of the second embodiment. Hereinafter, a description will be given of the operation of the X-ray CT apparatus 1B of the second embodiment according to the step number shown in FIG. 11. In FIG. 11, each step equivalent to the corresponding step in FIG. 4 of the first embodiment is assigned with the same step number as that of the first embodiment, and duplicate description is omitted.

In the flowchart of FIG. 11, a description will be given of cardiac imaging in which a scan mode is selected from a rotational scan and a plural-rotation scan.

In the step ST105, the shape specification function 511a specifies a shape of the heart based on a scanogram image.

In the next step ST201, the scan mode determination function 515b determines whether the entirety of the heart can be imaged by a rotational scan in the case of tilting the rotating body 25 or not. When it is determined that the entirety of the heart can be imaged by a rotational scan, the scan mode determination function 515b determines the scan mode to be a rotational scan and the processing circuitry 51b advances the processing to the step ST203. Conversely, when it is determined that the heart cannot be imaged by a rotational scan, the scan mode determination function 515b determines the scan mode to be a plural-rotation scan and the processing circuitry 51b advances the processing to the step ST205.

In the step ST203, the imaging condition setting function 513b sets imaging conditions of a rotational scan based on a shape of an anatomical site.

In the step ST205, the imaging condition setting function 513b sets imaging conditions of a plural-rotation scan based on a shape of an anatomical site.

Hereinafter, a description will be supplementarily given of the method of determining a scan mode to be performed by the imaging condition setting function 513b in the step ST201, with reference to FIG. 12 and FIG. 13.

Figure 12:
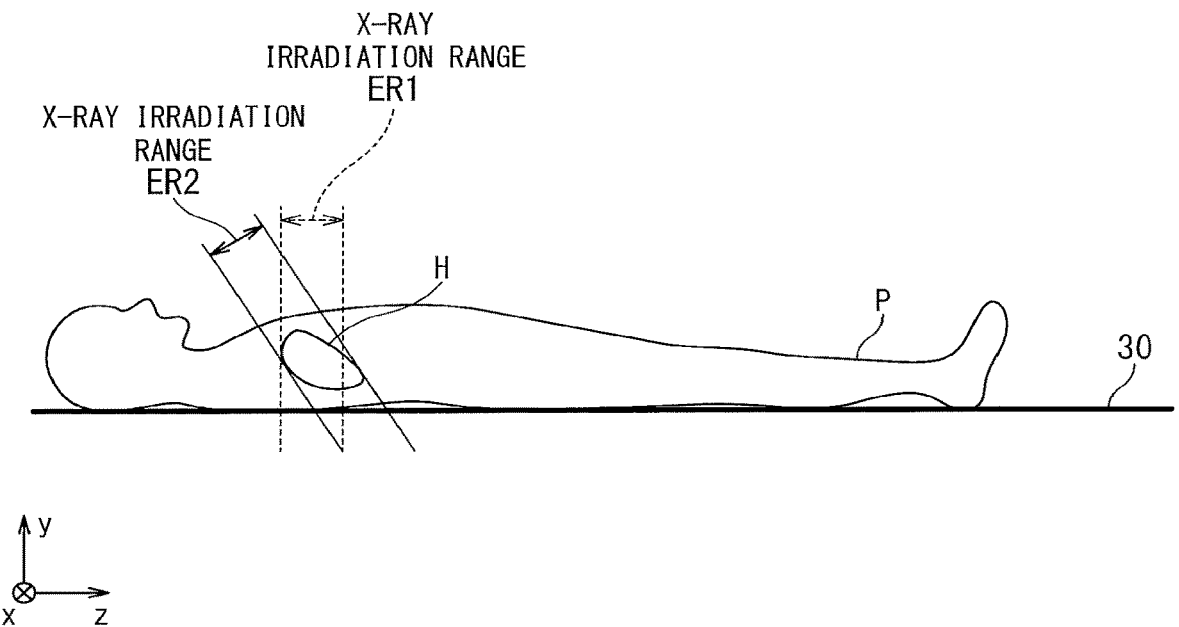
FIG. 12 is a schematic diagram illustrating a method of determining whether the entirety of a target region can be imaged by a rotational scan or not, in the second embodiment.

FIG. 12 is a schematic diagram illustrating a method of determining whether the entirety of a target region can be imaged by a rotational scan or not, in the second embodiment. FIG. 12 shows an X-ray irradiation range ER1 in the case of imaging the heart H under a rotational scan without setting a tilt angle, and also shows an X-ray irradiation range ER2 in the case of imaging the heart H under a rotational scan by setting a tilt angle.

A rotational scan is imaging in which an X-ray source rotates about the object P by 360 degrees or by 180 degrees plus an irradiation angle of an X-ray beam. When a tilt angle is not set, a part of the heart H is excluded from the X-ray irradiation range ER1 indicated by dashed lines as shown in FIG. 12. In other words, when a tilt angle is not set, it is impossible to image the entirety of the heart H by a rotational scan.

In general, when the heart is normal in terms of size, the entirety of this heart can be imaged by a rotational scan. Contrastively, when the heart is enlarged, a part of the enlarged heart is excluded from an X-ray irradiation range as shown in FIG. 12 and the entirety of this heart cannot be imaged by a rotational scan in some cases. In conventional technology, a plural-rotation scan is applied to such a case that the entirety of the heart cannot be imaged by a rotational scan.

However, in some cases, the entirety of the heart H is included in an X-ray irradiation range by tilting the rotating body 25 and the entirety of the heart H can be imaged by a rotational scan. The X-ray irradiation range ER2 indicated by solid lines in FIG. 12 shows an X-ray irradiation range in the case of tilting the rotating body 25. When the rotating body 25 is tilted, the entirety of the heart H is included in the X-ray irradiation range ER2 as shown in FIG. 12.

The scan mode determination function 515b of the second embodiment determines whether the entirety of the heart H is included in the X-ray irradiation range by tilting the rotating body 25 or not, and uses this determination result for determining whether a rotational scan can be applied or not. When it is determined that a rotational scan cannot be applied (i.e., the entirety of the heart H cannot be included in the X-ray irradiation range under a rotational scan), the scan mode determination function 515b selects a plural-rotation scan as a scan mode.

Figure 13:
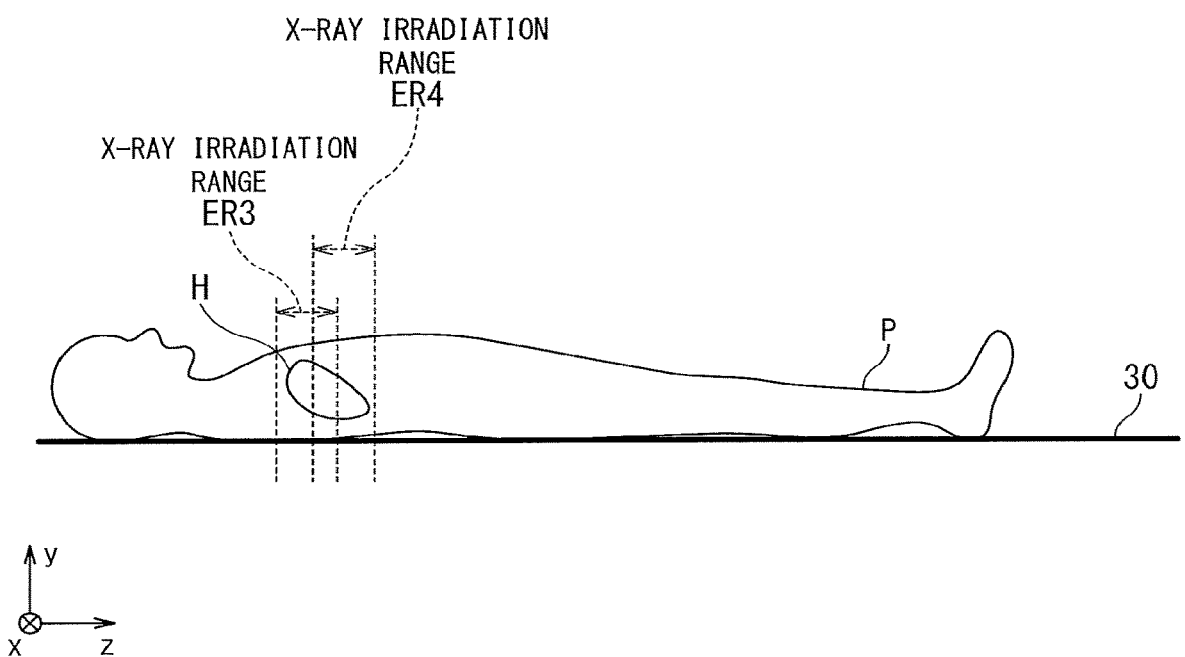
FIG. 13 is a schematic diagram illustrating X-ray irradiation ranges of a plural-rotation scan.

FIG. 13 is a schematic diagram illustrating X-ray irradiation ranges of a plural-rotation scan. A plural-rotation scan is a scan mode of combining plural rotational scans. As shown in FIG. 13, in a plural-rotation scan, in order to combine CT images acquired by the respective rotational scans, each rotational scan is performed such that the X-ray irradiation range ER3 is partially superimposed on the X-ray irradiation range ER4.

Thus, exposure dose can be suppressed in the case of imaging under a rotational scan than a case of imaging under a plural-rotation scan. The X-ray CT apparatus 1B of the second embodiment can apply a rotational scan to imaging of an anatomical site which is imaged by a plural-rotation scan in conventional technology, by specifying a shape of anatomical site. Thus, the X-ray CT apparatus 1B of the second embodiment can perform imaging with lower exposure dose than that of conventional technology.

When a part of the heart H is expected to be excluded from an X-ray irradiation range judging from a scanogram image, a user manually changes a scan mode in conventional technology. Contrastively, the X-ray CT apparatus 1B of the second embodiment automatically determines a scan mode based on the shape of the heart H. Thus, the X-ray CT apparatus 1B can perform imaging more efficiently and in shorter time than conventional technology.

Although a description has been given of the case where the heart is an anatomical site and a scan mode for this anatomical site is automatically determined, a scan mode for each anatomical site except the heart such as the brain can be automatically determined in a similar manner as described above.

Additionally, though a description has been given of the case where a rotational scan or a plural-rotation scan is alternatively selected as a scan mode in the flowchart of FIG. 11, determination of a scan mode is not limited to the operation shown in FIG. 11. There are various types of scan modes such as a helical scan, a vHP scan, a helical shuttle scan, a rotational scan, and a plural-rotation scan.

A helical shuttle scan is a type of helical scan in which a table is reciprocated. In a helical shuttle scan, it is also possible to change imaging conditions such as table moving velocity for each imaging range.

The scan mode determination function 515b may be configured to determine the optimum scan mode based on, e.g., a type and shape of an anatomical site specified from ALs which are acquired from a scanogram image. For instance, the scan mode determination function 515b may be configured to automatically determine a scan mode depending on a type of an organ depicted in a scanogram image. Additionally, the scan mode determination function 515b may determine a scan mode based on patient information and examination information and also based on a type and shape of an anatomical site specified from a scanogram image.

In the X-ray CT apparatus 1B of the second embodiment as described above, the effects of the first embodiment are also obtained, and it is further possible to set a scan mode with lower exposure dose on the basis of a shape of an anatomical site which is an imaging target.

According to an the X-ray CT apparatus in at least one of the above-described embodiments, it is possible to set imaging conditions by which exposure dose is lowered and satisfactory image quality is maintained.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An X-ray CT apparatus comprising:
a rotating body in which an X-ray source configured to radiate X-rays and an X-ray detector configured to detect the X-rays are housed; and
processing circuitry configured to
extract an anatomical landmark from a medical image of an object acquired by a first scan,
identify a shape of an anatomical site of the object to be examined based on the anatomical landmark,
calculate, based on the identified shape, multiple values corresponding to multiple tilt angles of simulated tilt scans of the object, wherein the multiple values respectively correspond to doses of radiation of a region of the object including the anatomical site scanned by the simulated tilt scans respectively corresponding to the multiple tilt angles,
determine, based on the calculated multiple values, a tilt angle among the multiple tilt angles such that (1) an entirety of the anatomical site is included in an imaging range and (2) a dose of the region is minimized, based on the shape of the anatomical site, and
perform a second scan based on scanning conditions including the determined tilt angle, wherein the second scan is performed with the rotating body tilted at the determined tilt angle.

2. The X-ray CT apparatus according to claim 1,
wherein the processing circuitry is configured to
extract a contour of the anatomical site based on pixel values of respective pixels around the anatomical landmark, and
specify the shape of the anatomical site based on the contour.

3. The X-ray CT apparatus according to claim 1,
wherein the processing circuitry is configured to compute the tilt angle by which a maximum value of X-ray absorption rate is minimized, based on pixel values of the medical image.

4. The X-ray CT apparatus according to claim 1,
wherein the processing circuitry is configured to select a scan mode of the second scan based on the shape of the anatomical site.

5. The X-ray CT apparatus according to claim 4,
wherein the processing circuitry is configured to select the scan mode of the second scan from scan-mode choices including at least a helical scan, a variable helical scan, a rotational scan, and a plural-rotation scan, the rotational scan being a scan mode in which a medical image is acquired by rotating the X-ray source about the object by 360 degrees, the plural-rotation scan being a scan mode in which movement of a table for placing the object and the rotational scan at each position of the table for scanning a part of an entire imaging range are repeated to scan the entire imaging range.

6. The X-ray CT apparatus according to claim 5,
wherein the processing circuitry is configured to compute the tilt angle by which the entire imaging range can be imaged under the rotational scan, based on the shape of the anatomical site.

7. The X-ray CT apparatus according to claim 1,
wherein the processing circuitry is configured to compute the tilt angle by which the imaging range is minimized and entirety of the anatomical site is included in an imaging range of the second scan, based on the shape of the anatomical site.

8. The X-ray CT apparatus according to claim 1,
wherein the processing circuitry is configured to
compute X-ray exposure dose to the object from the medical image of the object acquired by the first scan, and
set the scanning conditions by which the X-ray exposure to the object is minimized, based on the shape of the anatomical site.

9. The X-ray CT apparatus according to claim 1, wherein:
the X-ray detector includes a two-dimensional array type detector that has a two-dimensional detection area;
the region of the object corresponding to the two-dimensional detection area includes the anatomical site and ribs surrounding thereof; and
the processing circuitry is configured to
simulate tilt scans with AEC (auto exposure control) in which an X-ray intensity is automatically adjusted for each tilt scan, and
determine the tilt angle such that the dose of the region is minimized based on the simulated tilt scans with AEC.

10. The X-ray CT apparatus according to claim 9, wherein the processing circuitry is further configured to
compute the tilt angle by which a maximum value of X-ray absorption rate is minimized, based on pixel values of the medical image.

11. The X-ray CT apparatus according to claim 1, wherein:
the X-ray detector includes a two-dimensional array type detector that has a two-dimensional detection area; and
the processing circuitry is configured to
determine whether there is a tilt angle in which the entirety of the anatomical site is included within an imaging range of a half scan or a one rotational scan, when said tilt angle exists, perform the second scan for imaging the anatomical site by the half scan or the one rotational scan with the rotating body tilted at said tilt angle, and when said tilt angle does not exist, perform the second scan for imaging the anatomical site by a multiple rotational scan to cover the entirety of the anatomical site, with the rotating body tilted at the determined tilt angle.

\* \* \* \* \*